(12) United States Patent
Duan et al.

(10) Patent No.: US 9,371,304 B2
(45) Date of Patent: Jun. 21, 2016

(54) COMPOUND SEPARATED FROM MONASCUS-FERMENTED RICE, THE PREPARATION METHOD AND USES THEREOF

(75) Inventors: Zhenwen Duan, Beijing (CN); Shuren Guo, Beijing (CN); Xuemei Li, Beijing (CN); Chunli Liu, Beijing (CN)

(73) Assignee: Beijing Peking University WBL Biotech Co. Ltd, Beijing (CN)

( * ) Notice: Subject to any disclaimer, the term of this patent is extended or adjusted under 35 U.S.C. 154(b) by 258 days.

(21) Appl. No.: 13/983,048

(22) PCT Filed: Jan. 10, 2012

(86) PCT No.: PCT/CN2012/070169
§ 371 (c)(1),
(2), (4) Date: Jul. 31, 2013

(87) PCT Pub. No.: WO2012/103777
PCT Pub. Date: Aug. 9, 2012

(65) Prior Publication Data
US 2013/0310450 A1    Nov. 21, 2013

(30) Foreign Application Priority Data
Feb. 1, 2011    (CN) .......................... 2011 1 0033924

(51) Int. Cl.
*A61K 31/35*    (2006.01)
*C07D 309/30*    (2006.01)
(Continued)

(52) U.S. Cl.
CPC ............ *C07D 309/30* (2013.01); *A61K 31/366* (2013.01); *A61K 36/062* (2013.01); *A61K 36/899* (2013.01); *C07D 309/32* (2013.01); *A61K 2236/19* (2013.01)

(58) Field of Classification Search
CPC ...................................................... C07D 309/30
USPC .......................................................... 514/460
See application file for complete search history.

(56) References Cited

U.S. PATENT DOCUMENTS 5,627,068 A    5/1997  Kujumdzieva et al.
6,046,022 A *  4/2000  Zhang et al. .................... 435/41
(Continued)

FOREIGN PATENT DOCUMENTS

CN    101104003 A    1/2008
CN    101113146 A    1/2008
(Continued)

OTHER PUBLICATIONS

Komagata, Daisuke et al., "Biosynthesis of Monacolins: Conversion of Monacolin L to Monacolin J by a Monooxygenase of Monascus Ruber" The Journal of Antibiotics, Mar. 1989, vol. 42, No. 3, pp. 407-412.

Ma, Jiyuan, et al., "Constituents of Red Yeast Rice, a Traditional Chinese Food and Medicine" Journal of Agricultural and Food Chemistry, Oct. 13, 2000, vol. 48, pp. 5220-5225.

(Continued)

*Primary Examiner* — San-Ming Hui
(74) *Attorney, Agent, or Firm* — Honigman Miller Schwartz & Cohn LLP; Thomas A. Wootton; Jonathan P. O'Brien

(57) ABSTRACT

The present invention discloses a compound separated from *Monascus*-fermented rice, the preparation method and uses thereof. Specifically, the present invention discloses a compound represented by the Formula I, or a pharmaceutically acceptable salt thereof, wherein, $R_1$ is selected from the group consisting of hydrogen, hydroxyl, $C_{1-6}$ straight or branched alkoxyl, (II), (III) and (IV); $R_2$ is hydrogen or $C_{1-6}$ alkyl; $R_3$ is selected from the group consisting of hydrogen, hydroxyl and $C_{1-6}$ straight or branched alkoxyl. The present invention further discloses a pharmaceutical composition containing the compound. The compound of the present invention has HMG-CoA reductase inhibition effects.

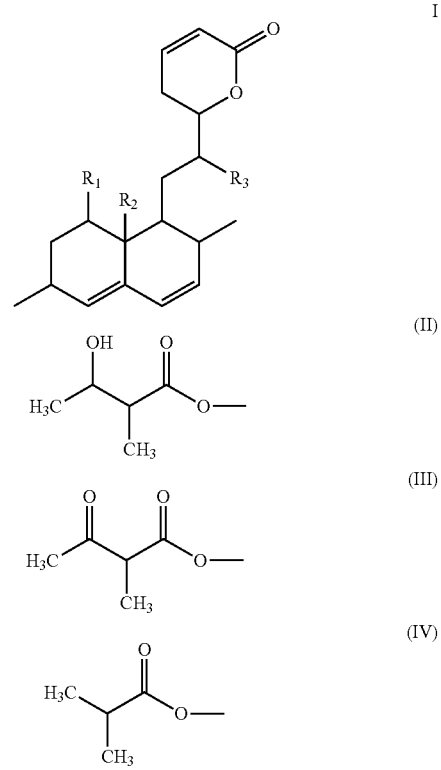

11 Claims, No Drawings

(51) Int. Cl.
  *A61K 31/366* (2006.01)
  *A61K 36/062* (2006.01)
  *C07D 309/32* (2006.01)
  *A61K 36/899* (2006.01)

(56) References Cited

U.S. PATENT DOCUMENTS 6,818,638 B2  11/2004  Baenteli et al.
7,238,348 B2   7/2007  Liang et al.

FOREIGN PATENT DOCUMENTS

JP  2002-537284  11/2002
JP  2003-521217   7/2003
JP  2005-333973  12/2005

OTHER PUBLICATIONS

Zhu, Lin et al. "Cytotoxic Dehydromonacolins from Red Yeast Rice." Journal of Agricultural and Food Chemistry, Jan. 3, 2012, vol. 60, No. 1, pp. 934-939.

Chairote et al., "Study on Cholesterol Lowering Compounds in Red Yeast Rice Prepared From Thai Glutinous Rice", Asian Journal of Food and Agro-Industry, 3(02):217-228, 2010.

Li Xm et al., "A new monacolin analogue from Xuezhikang capsule", Yao Xue Xue Bao (Acta Pharmaceutica Sinica), 46(5):564-567, 2011.

Li Yg et al., "Identification and chemical profiling of monacolins in red yeast rice using high-performance liquid chromatography with photodiode array detector and mass spectrometry", Journal of Pharmaceutical and Biomedical Analysis, 35(5):1101-1112, 2004.

* cited by examiner

COMPOUND SEPARATED FROM MONASCUS-FERMENTED RICE, THE PREPARATION METHOD AND USES THEREOF

TECHNICAL FIELD

The present invention pertains to pharmaceutical chemical field, and relates to a compound separated from *Monascus*-fermented rice, the preparation method and uses thereof. The present invention further relates to a pharmaceutical composition comprising the compound.

BACKGROUND

*Monascus*-fermented rice is a purple red rice koji prepared by using rice as raw material via fermentation with *Monascus*. *Monascus*-fermented rice is also called Danqu (丹曲) in ancient China, which is obtained via fermenting koji or mold (with *Monascus* as the main genus) on steamed rice; it is red color, and thus is also called red koji, red rice, or red wine dregs; and it is also called Fujian koji, Fujian rice, etc., because it is primarily produced in Fujian.

China has a long history of utilizing *Monascus*, and it has been used for koji making since Han Dynasty. *Monascus*-fermented rice is a traditional Chinese medicine as both food and drug. It had been widely used in the field of food coloring, wine-making, fermentation, Chinese medicine as early as in ancient times. "<Principle of Correct Proper Diet">(《饮膳正要》) has the recordation that *Monascus*-fermented rice is of "sweet taste and neutral nature and smooth in taste, non-toxic", "invigorating spleen, supplementing Qi, warming spleen and stomach"; <Compendium of Materia Medica>(《本草纲目》) has the recordation of "tonifying spleen, benefiting QI, warming spleen-stomach"; "Compendium of Materia Medica" (《本草纲目》) has recitations "sweet, warm, non-toxic", "capable of treating dysmenorrheal, extravasated blood after delivery, by grinding with rice wine and then drinking"; "<Addendum for Amplification on Materia Medica">(《本草衍义补遗》) has recordation of "activating blood, helping digestion, invigorating spleen and warming stomach, capable of treating red and white vaginal discharge and diarrhea, as well as traumatic injury", etc.

Since 1970s when Prof. Endo of Japan firstly separated a physiologically active substance, monacolin K from *Monascus* rubber, many researchers home and abroad discovered continually from *Monascus* metabolites physiologically active substances, including monacolin compounds, *monascus* pigment, pressure releasing component GABA and antioxidant component dimerumic acid, and some terpenoids being separated recently. With the development of modern biochemistry and pharmacology, functions of *Monascus*-fermented rice such as hypolipemic, loweringing blood pressure, hpyerglycemic, anti-obesity, anticancer, prophylaxis and treatment of senile dementia and osteoporosis are continuously revealed, which add more connotations to traditional *Monascus*-fermented rice.

"Xuezhikang" capsules are an alcohol extract of *Monascus*-fermented rice, which are rich in a series of natural statin compounds, monacolin K, dehydromonacolin K, monacolin L, dihydromonacolin K and other monacolin analogues. In addition, Xuezhikang capsules also contain pigment compounds, isoflavone compounds, sterol compounds, 20 kinds of amino acids, unsaturated fatty acids, and many trace elements. The isoflavone compounds mainly include genistein, daidzein, and glycitein, whose content is about 0.045%; sterol compounds are in an amount of about 0.3%, and mainly include ergosterol, stigmasterol, and sitosterol.

Contents of the Invention

With lots of experiments and inventive work, the inventors of the present invention obtain a new compound from *Monascus*-fermented rice or an alcohol extract thereof (e.g., dry powder of the content of Xuezhikang capsules), and surprisingly find that this compound has effective activity of inhibiting HMG-CoA reductase. Thus, the invention is provided as follows:

One aspect of the present invention relates to a compound of Formula I, or a pharmaceutically acceptable salt thereof,

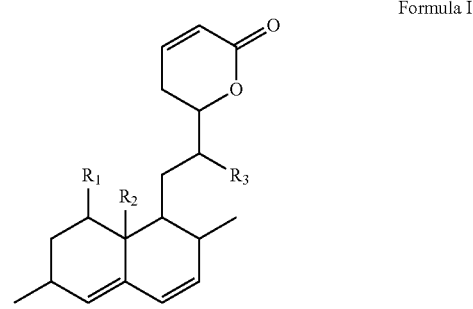

Formula I wherein, $R_1$ is selected from the group consisting of hydrogen, hydroxyl, $C_{1-6}$ straight or branched alkoxyl,

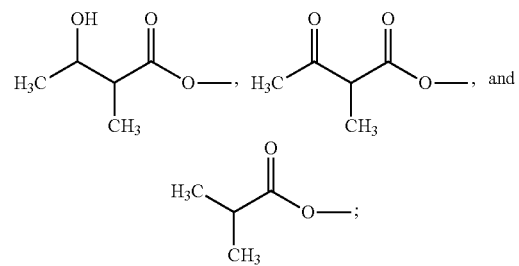

$R_2$ is hydrogen or $C_{1-6}$ alkyl;

$R_3$ is one or more same or different groups selected from the group consisting of hydrogen, hydroxyl, and $C_{1-6}$ straight or branched alkoxyl.

Specifically, said $C_{1-6}$ straight or branched alkoxyl is methoxy, ethoxy, $C_3$ straight or branched alkoxyl, $C_4$ straight or branched alkoxyl, $C_5$ straight or branched alkoxyl, or $C_6$ straight or branched alkoxyl. In one embodiment of the present invention, said $C_{1-6}$ straight or branched alkoxyl is $C_{1-3}$ straight or branched alkoxyl, for example methoxy, ethoxy, propoxy, or isopropoxy.

Specifically, said $C_{1-6}$ alkyl is methyl, ethyl, propyl, isopropyl, $C_4$ straight or branched alkyl, $C_5$ straight or branched alkyl, or $C_6$ straight or branched alkyl. In one embodiment of the present invention, said $C_{1-6}$ alkyl is $C_{1-3}$ alkyl, for example, methyl, ethyl, propyl, or isopropyl.

In one embodiment of the present invention, $R_1$ is 2 hydrogens, $R_2$ is hydrogen, and $R_3$ is 2 hydrogens, that is, the compound is shown in the following Formula II:

Formula II

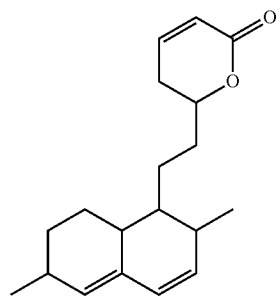

The present invention further relates to a hydrate or solvate of the compound of Formula I or Formula II above.

Another aspect of the present invention relates to a pharmaceutical composition, which comprises the compound of the present invention or a pharmaceutically acceptable salt thereof, and a pharmaceutically acceptable carrier or excipient.

In one embodiment of the present invention, said pharmaceutical composition is tablets, granules, capsules, pills, suppositories, pulvis, unguentums, drops, aerosols, inhalable powders, solutions, suspensions, buccal tablets, lyophilized powders, or emulsions, and can be commonly used preparations, sustained-release preparations, controlled-release preparations and various particulate delivery systems.

By using a pharmaceutical carrier known by those skilled in the art, a pharmaceutical composition containing an effective dose of the compound of the present invention can be prepared, for example, oral preparations (e.g., tablets, capsules, solutions or suspensions); injectable preparations (e.g., injectable solutions or suspensions, or injectable dry powders which can be immediately used by adding injection water before injection). Said carrier in the pharmaceutical composition includes: for oral preparations, binding agents (e.g., starch, usually corn, wheat or rice starch, gelatin, methylcellulose, sodium carboxymethylcellulose and/or polyvinylpyrrolidone), diluents (e.g., lactose, dextrose, sucrose, mannitol, sorbitol, cellulose, and/or glycerol), lubricants (e.g., silica, talc, stearic acid or salt thereof, usually magnesium stearate or calcium stearate, and/or polyethylene glycol), and if necessary, further comprising disintegrants such as starch, agar, alginic acid or salt thereof, usually sodium alginate, and/or effervesce mixtures, auxiliary solvents, stabilizers, suspending agents, pigments, correctants, etc.; for injectable preparations, preservatives, co-solvents, stabilizers, etc.; for topical preparations, matrixes, diluents, lubricants, preservatives, etc. The preparations can be administered via oral or parenteral routes (e.g., intravenous, subcutaneous, intraperitoneal or topical routes). If some drugs are unstable under stomach conditions, they can be formulated to form enteric-coated tablets.

Further another aspect of the present invention relates to a method for preparing compound of the present invention, comprising the following steps:
1) adding *Monascus*-fermented rice or an alcohol extract thereof to an organic solvent 1-10 times in volume, performing ultrasonic extraction at least one time, 10-60 minutes every time, combining extracting solutions, concentrating under reduced pressure to obtain a concentrated solution;
2) loading the concentrated solution on a silica gel column for separation, eluting in gradient manner with one or more selected from the group consisting of petroleum ether, ethyl acetate and methanol; and
3) subjecting the fraction containing the compound of Formula I or Formula H as obtained by elution in step 2) to the purification of silica gel column chromatography, sephadex LH-20 column chromatography, and high performance liquid chromatography to obtain the compound.

Optionally, the alcohol extract can be obtained by the following method: using 50%-100% ethanol or 50%-100% methanol 2-6 times in volume as solvent to perform ultrasonic extraction one or more times, 20-40 minutes every time, combining extracting solutions, removing solvent to obtain the alcohol extract.

Without being bound by theory, because Xuezhikang itself is an alcohol extract of *Monascus*-fermented rice, *Monascus*-fermented rice can be directly used as raw material, and the extracting steps are substantively the same as that of the dry powder of the content of Xuezhikang, whereas *Monascus*-fermented rice has a relatively lower content of the compound. The specific strains of *Monascus*-fermented rice are not particularly limited, and include any strains of *Monascus*. Xuezhikang capsules (e.g., those manufactured by Beijing Peking University WBL Biotech Co., Ltd.) are commercially available in hospitals or pharmacies.

Those skilled in the art can determine the fraction containing the compound of Formula I or Formula II (fraction with low polarity), for example, when the initial (eluting) solvent is petroleum ether:ethyl acetate (75:25 in volume ratio), the fraction containing the compound of Formula I or Formula II is the second column volume. When the initial solvent is petroleum ether:ethyl acetate (50:50) or has higher polarity, the fraction containing the compound of Formula I or Formula II is the first column volume.

According to the preparation method of (any aspect of) the present invention, wherein, in step 1), the organic solvent is one or more selected from the group consisting of n-hexane, dichloromethane, ethyl acetate, n-butanol, methanol, 50%-95% (v/v) methanol aqueous solution, ethanol, and 50%-95% (v/v) ethanol aqueous solution. Specifically, said methanol aqueous solution is 70% (v/v) methanol aqueous solution. Specifically, said ethanol aqueous solution is 70% (v/v) ethanol aqueous solution.

According to the preparation method of the present invention, in step 1), the added organic solvent is 2-6 times in volume, for example, the added organic solvent is 2, 3, 4, 5, or 6 times in volume.

According to the preparation method of the present invention, in step 1), the ultrasonic extraction is performed 3-5 times, 20-40 minutes every time; specifically, the ultrasonic extraction is performed 3, 4, or 5 times, 20-40 minutes every time.

According to the preparation method of the present invention, in step 1), the alcohol extract of *Monascus*-fermented rice is a dry powder of the content of Xuezhikang capsules.

According to the preparation method of the present invention, in step 2), petroleum ether and ethyl acetate in volume ratio of 75:25, 50:50, and 0:100 in order, and/or ethyl acetate and methanol in volume ratio of 100:0, 95:5, 70:30, and 50:50 in order are used for gradient elution. The number of silica gel columns is not specifically limited. In one embodiment of the present invention, silica gel columns of 200-300 mesh are used.

According to the preparation method of the present invention, in step 3), the silica gel column chromatography is eluted with petroleum ether-dichloromethane-methanol (10:10:1); optionally, the obtained fractions are analyzed with TLC and fractions with same analytic results are combined. Then, (for example, the second fraction thereof) is separated with sephadex LH-20 gel column using dichloromethane-methanol (1:1) as the mobile phase. According to TLC analysis results, fractions containing the compound are collected, concentrated and then purified with semi-preparative high performance liquid chromatography using acetonitrile-water solution (79:21) as the mobile phase, C18 semi-preparative chromatographic column (10×250 mm, 5 μm) as the immobile phase, and fractions of 16.08 min peak are collected, combined and concentrated to obtain the compound of the present invention.

The compound of Formula II of the present invention can be prepared by dehydration of monacolin L:

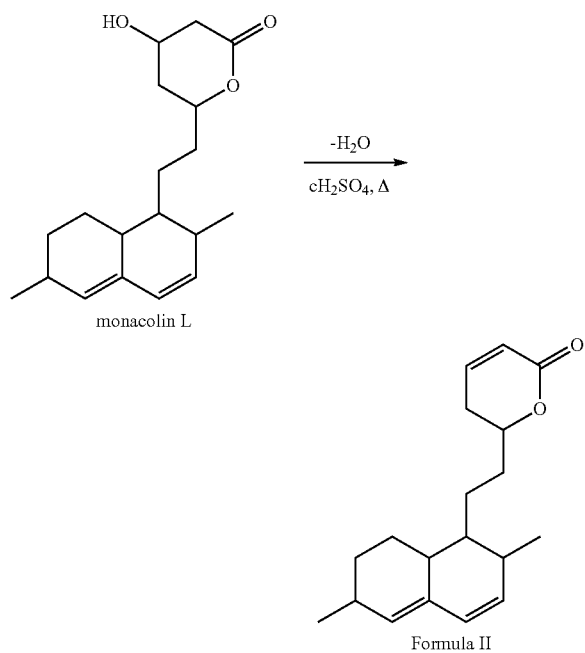

wherein, monacolin L can be commercially obtained, or can be prepared by the following method:
a. taking *Monascus*-fermented rice or an alcohol extract thereof (e.g., a dry powder of content of Xuezhikang capsules), performing ultrasonic extraction 3 times with n-hexane solvent 2-6 times in volume, 20-40 minutes every time, combining the extracting solutions, concentrating under reduced pressure to obtain a concentrated solution;
b. subjecting the concentrated solution of step a) to silica gel column chromatography separation, eluting in gradient manner with petroleum ether-ethyl acetate, collecting the fraction of petroleum ether-ethyl acetate (25:75); and
c. subjecting the fraction of petroleum ether-ethyl acetate (25:75) to sephadex LH-20 column chromatography and C-18 reversed phase silica gel column chromatography, and collecting the fraction containing monacolin L, and finally purifying with high performance liquid chromatography to obtain monacolin L.

Further another aspect of the present invention relates to an organic solvent extract of *Monascus*-fermented rice or a column chromatography fraction thereof, characterized in that the extract or the column chromatography fraction comprises the compound of Formula I or Formula II of the present invention or a pharmaceutically acceptable salt thereof; specifically, the organic solvent is selected from the group consisting of n-hexane, dichloromethane, ethyl acetate, n-butanol, methanol, 50%-95% (v/v) methanol aqueous solution, ethanol, and 50%-95% (v/v) ethanol aqueous solution; specifically, the chromatography is silica gel column chromatography and/or sephadex LH-20 column chromatography. The organic solvent extract of *Monascus*-fermented rice of the present invention can be obtained according to any one of the method for the preparation of the compound of the present invention; for example, the concentrated solution obtained in step 1) is also an organic solvent extract of the present invention.

Further another aspect of the present invention relates to use of the compound of the present invention or a pharmaceutically acceptable salt thereof in the manufacture of a HMG-CoA reductase inhibitor.

Further another aspect of the present invention relates to use of the compound of the present invention or a pharmaceutically acceptable salt thereof or the pharmaceutical composition or the organic solvent extract of *Monascus*-fermented rice of the present invention or the column chromatography fraction of the present invention in the manufacture of a medicament for treatment or prophylaxis of dyslipidemia, hyperlipemia, hypercholesterolemia, or atherosclerosis, for regulating or reducing cholesterol, or for adjunctive treatment of cardiovascular and cerebrovascular diseases caused by hyperlipidemia and atherosclerosis.

Further another aspect of the present invention relates to use of the compound of the present invention or a pharmaceutically acceptable salt thereof or the pharmaceutical composition or the organic solvent extract of *Monascus*-fermented rice or the column chromatography fraction of the present invention in the manufacture of a medicament for regulating blood lipid or reducing blood lipid.

Further another aspect of the present invention relates to use of the compound of the present invention or a pharmaceutically acceptable salt thereof or the pharmaceutical composition or the organic solvent extract of *Monascus*-fermented rice or the column chromatography fraction of the present invention in the manufacture of a medicament for regulating cholesterol or reducing cholesterol.

Further another aspect of the present invention relates to use of the compound of the present invention or a pharmaceutically acceptable salt thereof or the pharmaceutical composition or the organic solvent extract of *Monascus*-fermented rice or the column chromatography fraction of the present invention in the manufacture of a medicament for eliminating dampness to expel phlegm, activating blood circulation to dissolve accumulated stasis of blood, or invigorating spleen to promote digestion.

Further another aspect of the present invention relates to a method for the treatment or prophylaxis of dyslipidemia, hyperlipemia, hypercholesterolemia, or atherosclerosis, or for adjunctive treatment of cardiovascular and cerebrovascular diseases caused by hyperlipidemia and atherosclerosis in a mammal, comprising the step of administering an effective amount of the compound or the pharmaceutical composition or the organic solvent extract of *Monascus*-fermented rice or the column chromatography fraction of the present invention.

Further another aspect of the present invention relates to a method for regulating blood lipid or reducing blood lipid in a mammal as the subject, comprising the step of administering an effective amount of the compound or the pharmaceutical composition or the organic solvent extract of *Monascus*-fermented rice or the column chromatography fraction of the present invention.

Further another aspect of the present invention relates to a method for regulating cholesterol or reducing cholesterol in a mammal as the subject, comprising the step of administering an effective amount of the compound or the pharmaceutical composition or the organic solvent extract of *Monascus*-fermented rice or the column chromatography fraction of the present invention.

Further another aspect of the present invention relates to a method for eliminating dampness to expel phlegm, activating blood circulation to dissolve accumulated stasis of blood, or invigorating spleen to promote digestion in a mammal as the subject, comprising the step of administering an effective amount of the compound or the pharmaceutical composition or the organic solvent extract of *Monascus*-fermented rice or the column chromatography fraction of the present invention.

In the aforementioned or other treatment and/or prophylaxis, a compound of the present invention in a therapeutically and/or prophylactically effective amount can be used in the form of pure compound, or in the form of pharmaceutically acceptable esters or prodrugs thereof (if they exist). Alternatively, the compound can be administered via a pharmaceutical composition comprising the compound and one or more pharmaceutically acceptable excipients. The term a compound of the present invention in "effective amount" means that the compound is in an amount sufficient to achieve prophylactically and/or therapeutically reasonable ratio of effect/risk. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the specific compound used, the specific composition used, the age, body weight, general health status, gender and diet of patient, the administration time and route and excretory rate of the specific compound used, the drug(s) administered in combination or simultaneously with the specific compound, and similar factors well known in the art of medicine. For example, it is a common method in the art to increase the dose of compound gradually from a level lower than that for achieving desired therapeutical effects to a level enough to achieve the desired therapeutical effects. In general, the dose of the compound of Formula I for mammals especially for human can be 0.001-1000 mg/kg body weight per day, such as 0.01-100 mg/kg body weight per day, 0.01-10 mg/kg body weight per day.

Further another aspect of the present invention relates to a method for inhibiting HMG-CoA reductase in vivo or in vitro, comprising the step of administering an effective amount of the compound or the pharmaceutical composition or the organic solvent extract of *Monascus*-fermented rice or the column chromatography fraction of the present invention.

In the present invention, the concentration of methanol aqueous solution or ethanol aqueous solution is volume concentration (v/v).

Beneficial Effects of the Present Invention.

The compound of the present invention has effective activity of inhibiting HMG-CoA reductase, and can be used in the manufacture of a medicament for reducing blood lipid or reducing cholesterol.

Specific Models for Carrying Out the Invention

The present invention is further illustrated with the following examples, but those skilled in the art would understand that the following examples are merely used to illustrate the present invention, rather than to limit the protection scope of the present invention. For those technologies or conditions not specifically described in the examples, they were performed according to the technologies or conditions as described in the documents in the art or according to the product specifications. For those reagents and instruments whose manufacturers were not given, they were all conventional products commercially available in the market.

EXAMPLE 1

Preparation of Compound of the Present Invention 1) 1-2 kg of dry powder of the content of Xuezhikang capsules was taken, and ultrasonic extraction was performed 3 times with n-hexane of 2-6 times in volume as the solvent, 20-40 minutes every time, all the extracting solutions were combined, concentrated under reduced pressure to obtain a concentrated solution;
2) 50 g of the concentrated solution obtained in step 1) was loaded on a silica gel column to perform chromatographic separation, eluted in gradient manner with petroleum ether and ethyl acetate as well as methanol, in which the initial volume ratio of petroleum ether to ethyl acetate was 75:25;
3) the eluted fraction of petroleum ether-ethyl acetate (75:25) was divided into 3 parts, in which the first column volume part was H-1, the second column volume part was H-2, and the third column volume part was H-3;
4) 5.2 g of the H-2 part was subjected to the purification of silica gel column chromatography, sephadex LH-20 column chromatography, and semi-preparative high performance liquid chromatography, to obtain 10 mg of the compound.

In which, the step 4) could be carried out using the following method: 5.2 g of the H-2 part was subjected to silica gel column chromatography, eluted with petroleum ether-dichloromethane-methanol (10:10:1), analyzed with TLC and fractions with the same results were combined to obtain 6 parts, in which 1.38 g of the second part was separated with sephadex LH-20 gel column using dichloromethane-methanol (1:1) as the mobile phase. According to TLC analysis results, fractions containing the compound were collected, concentrated and then purified with semi-preparative high performance liquid chromatography, in which acetonitrile-water solution (79:21) was used as the mobile phase, C18 semi preparative chromatography column (10×250 mm, 5 µm) was used as the immobile phase, and fractions of 16.08 min peak were collected, combined and then concentrated to obtain 10 mg of the compound.

Those skilled in the art could understand that Xuezhikang itself is an alcohol extract of *Monascus*-fermented rice, so that *Monascus*-fermented rice could be directly used as the raw material, and the extraction steps were substantively identical to those for extracting dry powder of the content of Xuezhikang capsules, while the content of the compound in *Monascus*-fermented rice was lower than that in the dry powder of the content of Xuezhikang capsule.

EXAMPLE 2

Identification and Confirmation of Structure Formula of the Compound of Example 1

1. Physical and Chemical Data of the Compound

Colorless oily substance, optical rotation: $[\alpha]^{25}_D$+36.63 (c 0.636, $CH_2Cl_2$); UV spectrum had 3 maximum absorption peaks, which separately were $\lambda_{max}$ ($CH_2Cl_2$)=232.6 nm, 240.20 nm, 249.0 nm.

FT-IR spectrum showed that there were saturated hydrocarbons (2926 cm$^{-1}$) and ester carbonyl group (1717 cm$^{-1}$).

2. Identification of Molecular Formula

HR-ESI-MS showed m/z 287.1985 [M+H]$^+$ (calcd. 287.2006, err 2.1), which indicated that the molecular weight of the compound was 286.19. $^1$H-NMR and $^{13}$C-NMR showed that there were total 26 hydrogen signals and 19 carbon signals.

II DEPT showed that there were 2 quaternary carbons at 136.6 ppm and 164.6 ppm, and the quaternary carbon at 164.6 ppm was an ester carbonyl group. $^{13}$C-NMR showed that there was a signal of carbon connecting with oxygen at 78.3 ppm. Thus, the compound has 19 carbon atoms, 26 hydrogen atoms, 2 oxygen atoms, and molecular formula is $C_{19}H_{26}O_2$. The specific data are shown in Table 1.

TABLE 1

NMR data of the compound as prepared in Example 1

| No. | $^1$H-NMR, (ppm) | $^{13}$C-NMR, (ppm) | DEPT | HMBC ($^1$H to $^{13}$C), |
|---|---|---|---|---|
| 1 | 1.34 (1H, m) | 28.7 | CH | C7' |
| 2 | 2.07 (1H, m) | 34.9 | CH | C3 |
| 3 | 5.75 (1H, dd, J = 6.0, 9.5 Hz) | 133.0 | CH | C4, C4a |
| 4 | 5.94 (1H, d, J = 10.0 Hz) | 128.4 | CH | C3, C4a |
| 4a | — | 136.6 | C | — |
| 5 | 5.46 (1H, br s) | 130.5 | CH | C4 |
| 6 | 2.34 (1H, m) | 31.5 | CH | C4a, C8a |
| 7 | 1.44/1.73 (2H, m) | 24.4 | CH$_2$ | C8a |
| 8 | 1.20/1.80 (2H, m) | 22.6 | CH$_2$ | C4a, C1 |
| 8a | 1.44 (1H, m) | 41.9 | CH | — |
| 1' | — | 164.6 | C | — |
| 2' | 6.06 (1H, d, J = 10.0 Hz) | 121.5 | CH | C1' |
| 3' | 6.93 (1H, dt, J = 4.0, 10.0 Hz) | 145.0 | CH | C5', C4', C1' |
| 4' | 2.38 (2H, m) | 29.6 | CH$_2$ | C2', C3', C1' |
| 5' | 4.46 (1H, m) | 78.3 | CH | — |
| 6' | 1.54 (1H, m), 1.91 (1H, m) | 32.4 | CH$_2$ | — |
| 7' | 1.61 (1H, m), 1.71 (1H, m) | 29.3 | CH$_2$ | — |
| 2-Me | 1.01 (3H, d, J = 7.0 Hz) | 21.2 | CH$_3$ | C1, C3 |
| 6-Me | 0.92 (3H, d, J = 7.0 Hz) | 13.9 | CH$_3$ | C6, C5 |

Notation: "—" represents absence of correlated signals.

3. Identification of Structure

UV spectrum showed 3 maximum absorption peaks at 232.6 nm, 240.20 nm and 249.0 nm, which indicated that this compound is a typical statin compound. The carbon spectra of the compound ($^{13}$C-NMR and DEPT) showed there were 19 carbon atoms, very similar to the statin compound monacolin L. By comparing the molecular weight and molecular formula of these two compounds, the present invention compound had one less water molecule. By further comparison of carbon spectra of the two compounds, it was found that the present invention compound had two more signals, C2' and C3' (121.5 ppm and 145.0 ppm) in alkene carbon region, and had one less carbon connecting with oxygen than monacolin L. In comparison of the $^1$H-NMR of the two compounds, it was found that there were two more alkene hydrogens H2' and H3' (6.06 ppm and 6.93 ppm) in the lower field region. In sum, this compound has one less water molecule and one more double bond than monacolin L. Hence, it can be determined that the compound is possibly the dehydration product of monacolin L (structure shown in Formula III).

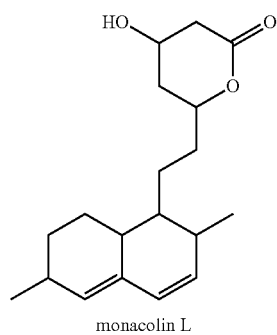

Formula III monacolin L

Further analysis of HMBC correlated signal spectra of the compound (as shown in Formula IV) showed that both H2' and H3' had correlated signals with C1' (164.6 ppm), besides, H3' had correlated signals with C4' (29.6 ppm) and C-5' (78.5 ppm). This indicated that the two extra alkene carbons (C2'=C3') were located between carbonyl group and C4'-O5', which also confirmed the above analysis that this compound was dehydrated monacolin L.

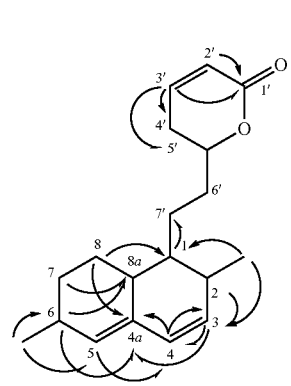

Formula IV

The above analysis suggested that it was: 6-(2-(2,6-dimethyl-1,2,6,7,8,8a-hexahydronaphthalene)ethyl)-5,6-dihydropyran-2-one, that was (6-(2-(2,6-dimethyl-1,2,6,7,8,8a-hexahydronaphthalen-1-yl)ethyl)-5,6-dihydropyran-2-one), of which the structure formula was shown in the following Formula II:

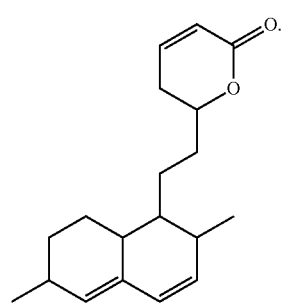

Formula II

EXAMPLE 3

Test of Inhibiting Activity of HMG-CoA Reductase

1. Experimental Materials

The compound of Formula II prepared according to Example 1.

monacolin L (purchased or prepared according to the method of the contents of the present invention)

Standard Sample of Lovastatin (Purchased from Sigma)

Microsomes of rat liver (HMG-CoA reductase) were purchased, or prepared according to the following method: liver of a male rat was taken out, washed with KESD buffering solution, then centrifuged at 1,200 g for 15 min, the supernatant was taken out, and then centrifuged at 105,000 g for 90 min twice, and a centrifugation precipitate was collected. The centrifugation precipitate was added with 8.3% glycerol, heated with 37° C. bath for 1 h. The microsomes of rat liver were purified with saturated ammonium sulfate and the 33-50% purified fraction was collected. The obtained microsomes of rat liver were stored in refrigerator at −80° C.

Potassium chloride, potassium dihydrogen phosphate, ethylene diamine tetraacetic acid, dithiothreitol (all purchased from Beijing Chemical Reagent Co., Ltd.)

Nicotinamide adenine dinucleotide (NADPH) (purchased from Merck) 3-hydroxy-3-methylglutaryl coenzyme A (HMG-CoA) and cremophore EL (purchased from Sigma).

2. Experimental Method

The compound as prepared according to Example 1 was dissolved with 50% cremophore EL ethanol solution, and the concentration was 2 mg/mL; the total volume of the system was determined and it was 250 µL, and the concentration of each component was: potassium chloride 200 mM, potassium dihydrogen phosphate 160 mM, ethylene diamine tetraacetic acid 4 mM, dithiothreitol 10 mM, concentrations of two substrates, nicotinamide adenine dinucleotide and 3-hydroxy-3-methylglutaryl coenzyme A, 200 µM and 50 µM separately, pH6.8, addition of enzyme 30 µL, enzyme inhibitor 5 µL, blank control group 5 µL (solvent for dissolving sample). The dynamic change of $OD_{340}$ was detected with Versamax ELIASA at 37° C. The rate of decline (represented with slope value) of $OD_{340}$ within 5 min was used to evaluate the activity of HMG-CoA reductase, and then to evaluate the activity of enzyme inhibitor.

3. Test Results

The test results are shown in Table 2.

TABLE 2

Test results of enzyme inhibitor activity

| Sample Name | Inhibitor concentration (mg/mL) | Inhibitor volume (µL) | Final concentration (µg/mL) | Slope | Inhibition rate (%) |
|---|---|---|---|---|---|
| Blank control | — | — | — | 9.971 | — |
| Lovastatin | 1.72 | 5 | 34 | 6.022 | 39.6 |
| monacolin L | 1.5 | 5 | 30 | 7.279 | 27.0 |
| The compound of Formula II as prepared according to Example 1 | 2.0 | 5 | 40 | 7.344 | 26.3 |

* blank control was solvent.

Lovastatin and monacolin L were positive controls.

It can be seen from Table 2, the compound of Formula II as prepared according to Example 1 had effective activity for inhibiting HMG-CoA reductase.

Although the specific embodiments of the present invention have been described in details, those skilled in the art would understand that these details can be modified or substituted according to the disclosed teachings, and all these changes are within the protection scope of the present invention. The whole scope of the present invention is defined by the appending claims and any of the equivalents thereof.

What is claimed is:

1. A compound shown in Formula I, or a pharmaceutically acceptable salt thereof, Formula I wherein, $R_1$ is selected from the group consisting of hydrogen, hydroxyl, $C_{1-6}$ straight or branched-alkoxyl, $R_2$ is hydrogen or $C_{1-6}$ alkyl;

$R_3$ is one or more same or different groups selected from the group consisting of hydrogen, hydroxyl, and $C_{1-6}$ straight or branched alkoxyl.

2. The compound according to claim 1, or a pharmaceutically acceptable salt thereof, which is shown in the following Formula II:

Formula II

3. A pharmaceutical composition, which consists essentially of the compound of claim 1 or a pharmaceutically acceptable salt thereof, and a pharmaceutically acceptable excipient.

4. The pharmaceutical composition according to claim 3, which is in the form of tablets, granules, capsules, pills, suppositories, pulvis, unguentums, drops, aerosols, inhalable powders, solutions, suspensions, buccal tablets, lyophilized powders, or emulsions.

5. A method for preparing the compound of claim 1 comprising the following steps:
   1) adding *Monascus*-fermented rice or an alcohol extract thereof to an organic solvent 1-10 times in volume, performing ultrasonic extraction at least one time, 10-60 minutes every time, combining the extracting solutions, concentrating under reduced pressure to obtain a concentrated solution;
   2) loading the concentrated solution on a silica gel column for separation, eluting in gradient manner with one or more eluent selected from the group consisting of petroleum ether, ethyl acetate and methanol; and
   3) subjecting the fraction containing the compound of Formula I or Formula II as obtained by elution in step 2) to the purification of silica gel column chromatography, sephadex LH-20 column chromatography, and high performance liquid chromatography to obtain the compound.

6. The method according to claim 5, which meets any one of the following items (1)-(8):
   (1) in step 1), said organic solvent is one or more selected from the group consisting of n-hexane, dichloromethane, ethyl acetate, n-butanol, methanol, 50%-95% (v/v) methanol aqueous solution, ethanol, and 50%-95% (v/v) ethanol aqueous solution;
   (2) in step 1), the added organic solvent is of 2-6 times in volume;
   (3) in step 1), the ultrasonic extraction is performed 3-5 times, 20-40 minutes every time;
   preferably, in step 1), the ultrasonic extraction is performed 3 times, 20-40 minutes every time;
   (4) in step 1), said alcohol extract of *Monascus*-fermented rice is a dry powder of the content of Xuezhikang; and
   (5) in step 2), petroleum ether and ethyl acetate in volume ratio of 75:25, 50:50, and 0:100 in order, and/or ethyl acetate and methanol in volume ratio of 100:0, 95:5, 70:30, and 50:50 in order are used for gradient elution;
   (6) in step 3), said silica gel column chromatography is eluted with petroleum ether-dichloromethane-methanol (10:10:1);
   (7) in step 3), the sephadex LH-20 gel column for separation uses dichloromethane-methanol (1:1) as the mobile phase;
   (8) in step 3), said purification of semi-preparative high performance liquid chromatography uses acetonitrile-water solution (79:21) as the mobile phase, C18 semi-preparative chromatography column as the immobile phase, and fractions of 16.08 min chromatographic peak are collected and concentrated.

7. A method for the treatment or prophylaxis of dyslipidemia, hyperlipemia, hypercholesterolemia, or atherosclerosis, or for adjunctive treatment of cardiovascular and cerebrovascular diseases caused by hyperlipidemia and atherosclerosis in a mammal, comprising a step of administering an effective amount of the pharmaceutical composition of claim 3.

8. A method for regulating blood lipid or reducing blood lipid in a mammal as the subject, comprising a step of administering an effective amount of the pharmaceutical composition of claim 3.

9. A method for regulating cholesterol or reducing cholesterol in a mammal as the subject, comprising a step of administering an effective amount of the pharmaceutical composition of claim 3.

10. A method for eliminating dampness to expel phlegm, activating blood circulation to dissolve accumulated stasis of blood, or invigorating spleen to promote digestion in a mammal as the subject, comprising a step of administering an effective amount of the pharmaceutical composition of claim 3.

11. A method for inhibiting HMG-CoA reductase in vivo or in vitro, comprising a step of administering an effective amount of the pharmaceutical composition of claim 3.

* * * * *